(12) United States Patent
Gerber et al.

(10) Patent No.: US 6,450,420 B1
(45) Date of Patent: Sep. 17, 2002

(54) DISINFECTANT SPRAYING APPARATUS

(75) Inventors: Donavon G Gerber; Andrew M Holverson; Rodney J. La Combe, all of Monroe, WI (US)

(73) Assignee: Monroe Truck Equipment Inc., Monroe, WI (US)

( * ) Notice: Subject to any disclaimer, the term of this patent is extended or adjusted under 35 U.S.C. 154(b) by 0 days.

(21) Appl. No.: 09/840,452

(22) Filed: Apr. 23, 2001

(51) Int. Cl.$^7$ ............................................... A01G 25/09
(52) U.S. Cl. .................... 239/172; 239/71; 239/147; 239/159; 239/163; 239/722; 239/723; 239/754
(58) Field of Search ............................ 239/172, 71, 73, 239/147, 159, 163, 722, 723, 754

(56) References Cited

U.S. PATENT DOCUMENTS

| | | | | |
|---|---|---|---|---|
| 1,448,910 A | * | 3/1923 | Bolger | 239/172 |
| 3,512,714 A | * | 5/1970 | Phelps et al. | 239/172 |
| 4,771,822 A | * | 9/1988 | Barbosa | 123/41.01 |
| 5,267,696 A | * | 12/1993 | Balmer | 239/172 |
| 6,065,686 A | * | 5/2000 | Betts-Williams et al. | 239/172 |

OTHER PUBLICATIONS

Fact Sheet U.S. Department of Agriculture Animal & Plant Health Inspection Services Mar. 2001 3 Pages.
APHIS. Back Grounder Jul. 2000. 2 Pages.
APHIS. Fact Sheet Sep. 1999 2 Pages.
APHIS Fact Sheet Mar. 2001 3 Pages.
APHIS Fact Sheet Jan. 2001 4 Pages.
APHIS Fact Sheet Mar. 2001 2 Pages.
APHIS Fact Sheet Jan. 2001 4 Pages. Q & A Bovine Encephalopathy (BSE).
APHIS. Fact Sheet Mar. 2001. 10 Pages.
APHIS Fact Sheet Mar. 2001 Foot & Mouth Disease. Q & A's 2 Pages.
APHIS Fact Sheet Aug. 2000 Vermont Sheep Q & A. 14 Pages.
The Monroe Times Farmers Look at Disease's Local Impact Apr. 18, 2001. 2 Pages.

* cited by examiner

Primary Examiner—Robin O. Evans
(74) Attorney, Agent, or Firm—David J. Archer

(57) ABSTRACT

A disinfectant spraying apparatus is disclosed for mounting on a vehicle for spraying disinfectant on each tire of a vehicle before and after entering a livestock farm. The apparatus includes a container for containing the disinfectant, the container being mounted on the vehicle. A pump is disposed in fluid communication with the container for pumping the disinfectant from the container and a motor is provided for driving the pump. A manually operated switch is provided for selectively connecting the motor to a source of power such that when the switch is disposed in an operative disposition thereof, the motor is energized so that the motor drives the pump for generating a flow of the disinfectant downstream from the pump. A flow splitter is included for splitting the flow of the disinfectant pumped by the pump from the container such that the flow is split into a plurality of flow lines.

21 Claims, 5 Drawing Sheets

DISINFECTANT SPRAYING APPARATUS

BACKGROUND OF THE INVENTION

1. Field of the Invention

The present invention relates to a disinfectant spraying apparatus for mounting on a vehicle. More specifically, the present invention relates to a disinfectant spraying apparatus for mounting on a vehicle for spraying disinfectant on each tire of a vehicle before and after entering a livestock farm.

2. Background Information

With the latest outbreak of foot-and-mouth disease in the United Kingdom over 1.5 million animal were destroyed. Foot-and-mouth disease is an extremely contagious disease caused by a virus that can survive for up to 6 months in wet manure and for 39 days in animal urine. The virus can be transported through milk, saliva and even an animal's breath. Statistics indicate that pigs produce the virus 1000 times more than cows. Typically, the animal will carry the disease for two weeks before any outward sign of the disease shows up. The signs of the disease include fever, blisters, lameness, excessive salivation and in cows, a drop in milk production.

In the United States of America, the last outbreak of foot-and-mouth disease was recorded in 1929 in California. However, farmers and others are extremely concerned and for good reason, that the disease could be spread by persons visiting farms and transporting the virus from one farm to another on the tires of vehicle or on the footwear of drivers and passengers visiting farms.

Accordingly, the present invention provides an apparatus which greatly reduces the risk of germs being transported from farm to farm on vehicle tires contaminated with infected manure or urine or on the boots of drivers of such vehicles.

More specifically, the present invention includes a tank for containing disinfectant and a pumping system for controllably pumping the disinfectant and spraying the same onto each of the tires of a vehicle before and after entering a farm.

The present invention also provides a device for spraying the footwear of the driver before entering and leaving the farm particularly if the driver needs to get out of the vehicle while visiting the farm.

The present invention finds particular application as a retrofit device for securement to mail delivery vehicles, vehicles used by utility meter reading personnel and farm supply merchants. However, ideally, the spraying equipment would be provided on all vehicles used for transportation between farms.

Therefore, it is a primary feature of the present invention to provide a disinfectant spraying apparatus that overcomes any problems associated with prior art arrangements designed to avoid the spread of contagious disease.

Another feature of the present invention is the provision of a disinfectant spraying apparatus that inhibits the spread of animal diseases.

A further feature of the present invention is the provision of a disinfectant spraying apparatus of relatively low cost.

Another feature of the present invention is the provision of a disinfectant spraying apparatus that permits spraying of each tire of a vehicle.

Other features and advantages of the present invention will be readily apparent to those skilled in the art by a consideration of the detailed description of a preferred embodiment of the present invention contained herein.

SUMMARY OF THE INVENTION

The present invention relates to a disinfectant spraying apparatus for mounting on a vehicle for spraying disinfectant on each tire of the vehicle before and after entering a livestock farm. The apparatus includes a container for containing the disinfectant, the container being mounted on the vehicle. A pump is disposed in fluid communication with the container for pumping the disinfectant from the container and a motor is provided for driving the pump. A manually operated switch is provided for selectively connecting the motor to a source of power such that when the switch is disposed in an operative disposition thereof, the motor is energized so that the motor drives the pump for generating a flow of the disinfectant downstream from the pump. A flow splitter is included for splitting the flow of the disinfectant pumped by the pump from the container such that the flow is split into a plurality of flow lines. Each flow line of the plurality of flow lines has an upstream and a downstream end. An indicator is disposed between the upstream and downstream ends of each flow line for indicating flow of the disinfectant through the flow line. Also, a spray nozzle is disposed adjacent to the downstream end of each flow line, the nozzle being located in the vicinity of a wheel of the vehicle so that the vehicle wheel is initially sprayed with the disinfectant prior to entry of the vehicle into the farm for inhibiting the spread of contagious disease into the farm and for further spraying the vehicle wheel when the vehicle leaves the farm.

In a more specific embodiment of the present invention, the container is of rectangular configuration and is fabricated from polypropylene. Also, the container has a capacity within the range 6–12 gallons. The pump has a flow capacity within the range 2–4 gallons per minute and includes a diaphragm. Moreover, the motor is a 12 volt D.C. electric motor.

Additionally, the spraying apparatus further includes a control panel so that the manually operated switch can be mounted on the control panel. Also, the indicator is mounted on the control panel. Preferably, the manually operated switch includes a push button actuator.

The spraying apparatus also includes a timer which is electrically connected to the manually operated switch so that the timer throws the switch from the operative disposition to an inoperative disposition thereof after a period of time. More specifically, the timer includes an adjuster for adjusting the period of time.

Furthermore, the flow splitter splits the flow into four flow lines for spraying each wheel of the vehicle. Also, the indicator is a LED indicator light.

The spray nozzle includes a first fan pattern spray for spraying an outer wall and tread of one of the tires and a second fan pattern spray is positioned for spraying an inner wall and tread of the tire. Each of the fan pattern sprays includes a shield for protecting the fan pattern spray. Also, each of the fan pattern sprays includes an anti-drip check valve which preferably is a one way flow valve for maintaining the fan pattern spray primed with the disinfectant.

Many modifications and variations of the present invention will be readily apparent to those skilled in the art by a consideration of the detailed description contained hereinafter taken in conjunction with the annexed drawings which show a preferred embodiment of the present invention. However, such modifications and variations fall within the spirit and scope of the present invention as defined by the appended claims.

BRIEF DESCRIPTION OF THE DRAWINGS

Similar reference characters refer to similar parts throughout the various views of the present invention.

DETAILED DESCRIPTION OF THE DRAWINGS

Figure 1:
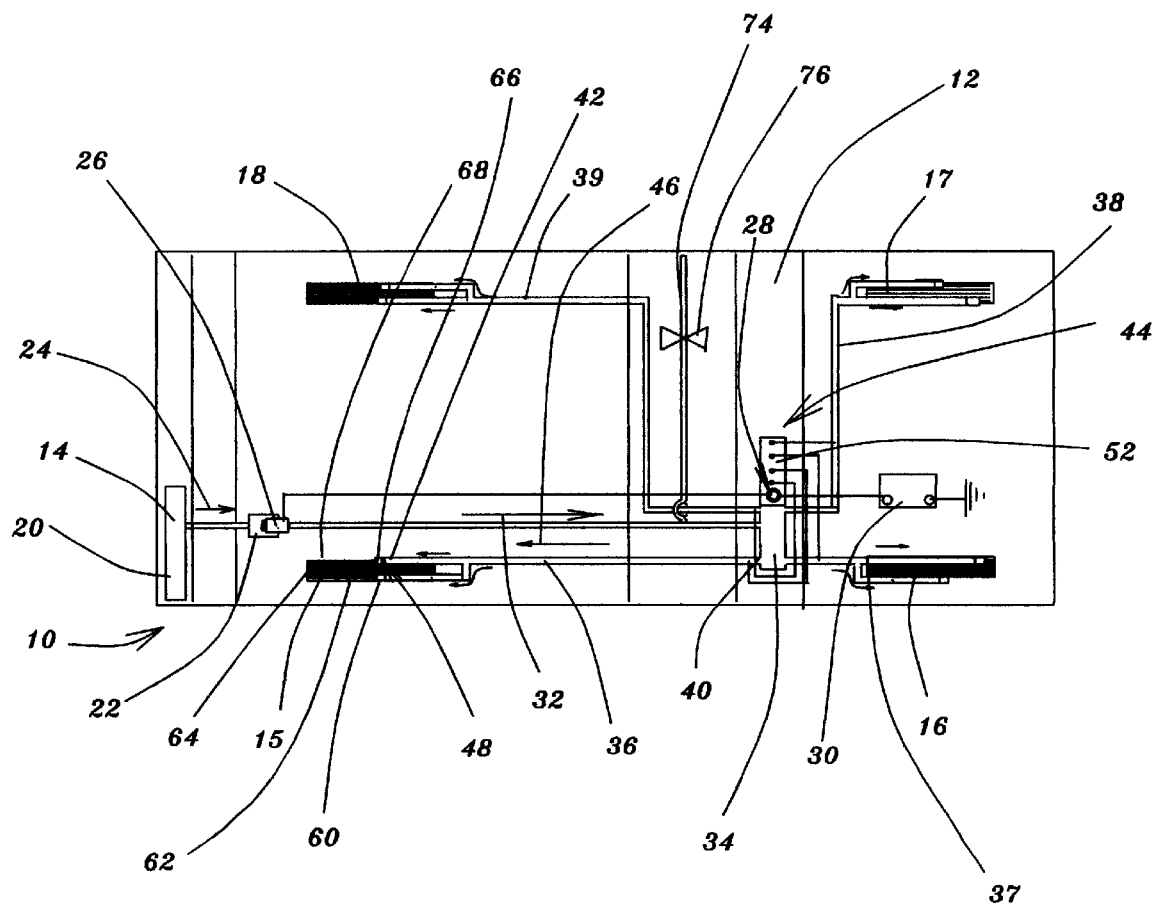
FIG. 1 is a top sectional view of a disinfectant spraying apparatus mounted on a vehicle according to the present invention.

FIG. 1 is a top sectional view of a disinfectant spraying apparatus generally designated 10 according to the present invention. As shown in FIG. 1, the apparatus 10 is mounted on a vehicle 12 for spraying disinfectant 14 on each tire 15, 16, 17 and 18 respectively of the vehicle 12 before and after entering a livestock farm. The apparatus 10 includes a container 20 for containing the disinfectant 14, the container 20 being mounted on the vehicle 12. A pump 22 is disposed in fluid communication with the container 20 for pumping the disinfectant 14 from the container 20 as indicated by the arrow 24. A motor 26 is provided for driving the pump 22. A manually operated switch generally designated 28 is provided for selectively connecting the motor 26 to a source of power 30 such that when the switch 28 is disposed in an operative disposition thereof, the motor 26 is energized so that the motor 26 drives the pump 22 for generating a flow of the disinfectant, as indicated by the arrow 32, downstream from the pump 22. A flow splitter 34 is included for splitting the flow 32 of the disinfectant 14 pumped by the pump 22 from the container 20 such that the flow 32 is split into a plurality of flow lines 36, 37, 38 and 39. Each flow line such as flow line 36 of the plurality of flow lines 36–39 has an upstream and a downstream end 40 and 42 respectively. An indicator generally designated 44 is connected between the upstream and downstream ends 40 and 42 respectively of each of the flow lines 36–39 for showing fluid flow, as indicated by the arrow 46, of the disinfectant 14 through the flow line such as line 36. Also, a spray nozzle generally designated 48 is disposed adjacent to the downstream end 42 of each flow line such as flow line 36 of the plurality of flow lines 36–39. The nozzle 48 is located in a vicinity of a tire such as tire 15 of the vehicle 12 so that the vehicle tire 15 and each of the other tires 16–18 is initially sprayed with the disinfectant 14 prior to entry of the vehicle 12 into the farm for inhibiting the spread of contagious disease into the farm and for further spraying the vehicle tires when the vehicle 12 leaves the farm.

Figure 2:
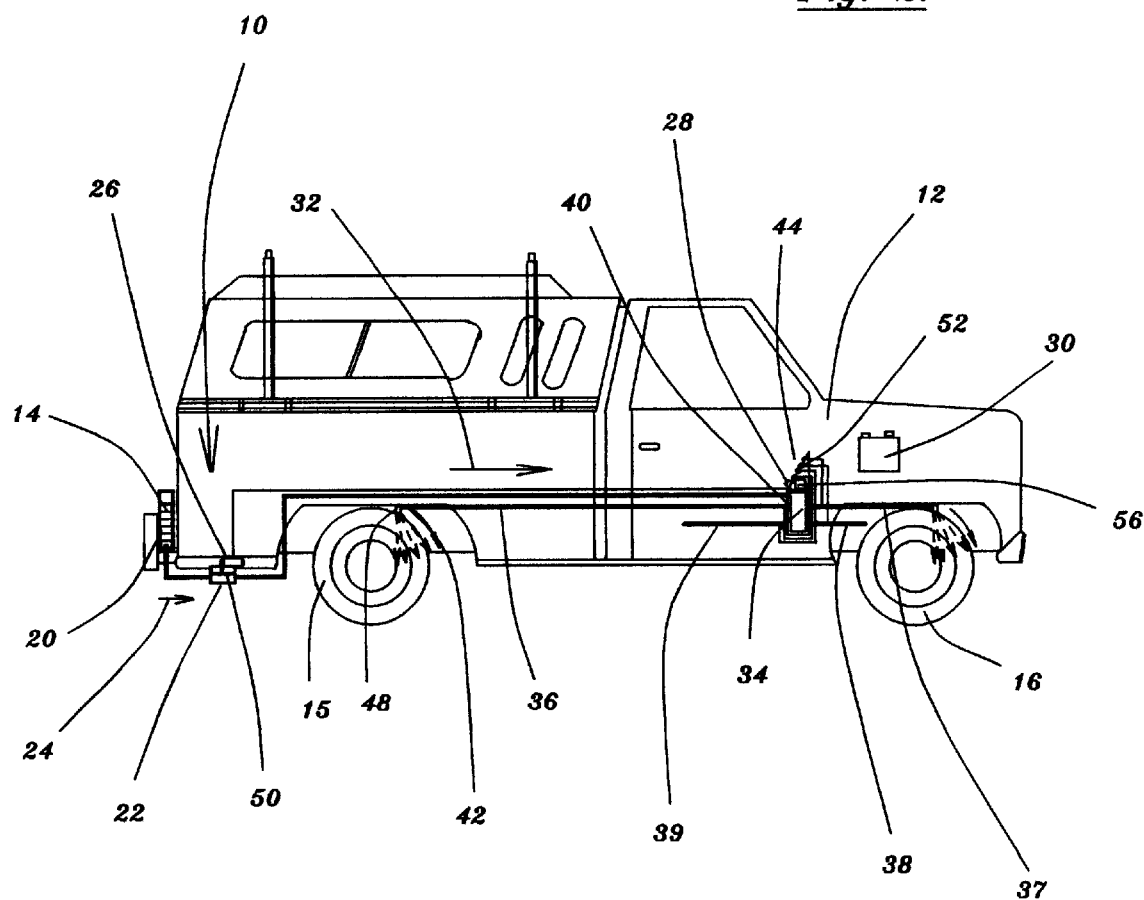
FIG. 2 is a side elevational view of the apparatus shown in FIG. 1.

FIG. 2 is a side elevational view of the apparatus shown in FIG. 1. As shown in FIG. 2, the container 20 is of rectangular configuration and is fabricated from polypropylene. Also, the container 20 has a capacity within the range 6–12 gallons and preferably has a capacity of 9 gallons. The pump 22 has a flow capacity within the range 2–4 gallons per minute and preferably has a flow rate of 3 gallons per minute and includes a diaphragm 50. Moreover, the motor 26 is preferably a 12 volt D.C. electric motor. The disinfectant can be of the type known as Virkon-S, Phenol or Chlorhexidine or any other suitable disinfectant.

Additionally, the spraying apparatus 10 further includes a control panel 52 so that the manually operated switch 28 is mounted on the control panel 52. Also, the indicator 44 is mounted on the control panel 52.

Figure 3:
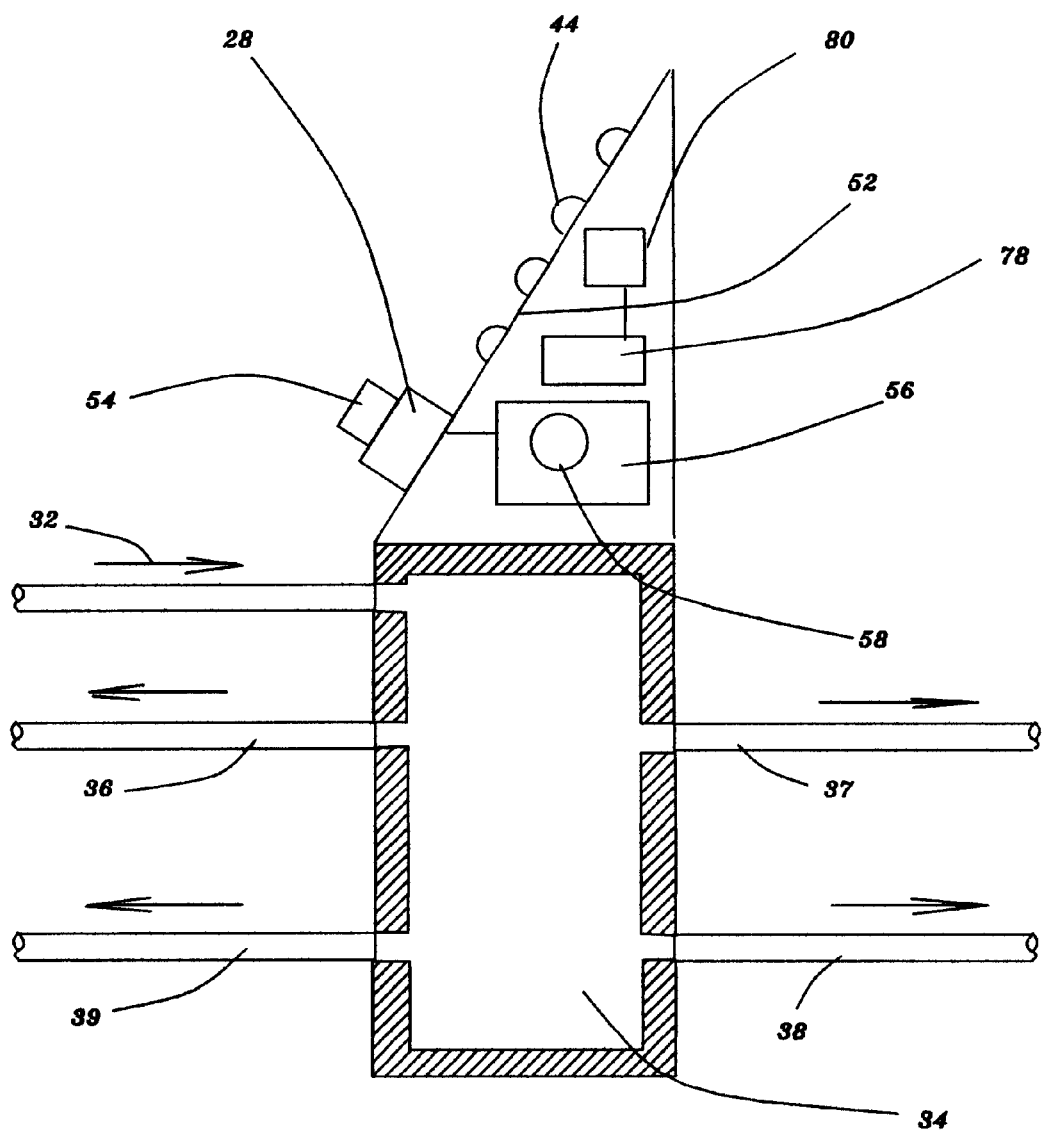
FIG. 3 is an enlarged side elevational view partially in section of the splitter and control panel shown in FIG. 1.

FIG. 3 is an enlarged view partially in section of the control panel 52. As shown in FIG. 3, the manually operated switch 28 includes a push button actuator 54 and the spraying apparatus 10 also includes a timer 56 which is connected to the manually operated switch 28 so that the timer 56 throws the switch 28 from the operative disposition to an inoperative disposition thereof after a period of time. More specifically, the timer 56 includes an adjuster 58 for adjusting the period of time.

Furthermore, the flow splitter 34 splits the flow 32 into the four flow lines 36–39 for spraying each tire 15–18 of the vehicle 12. Also, the indicator 44 is a LED indicator light.

As shown in FIG. 1, the spray nozzle generally designated 48 includes a first fan pattern spray 60 for spraying an outer wall 62 and tread 64 of one of the tires 15–18 such as tire 15 and a second fan pattern spray 66 for spraying an inner wall 68 and tread 64 of the tire 15.

Figure 4:
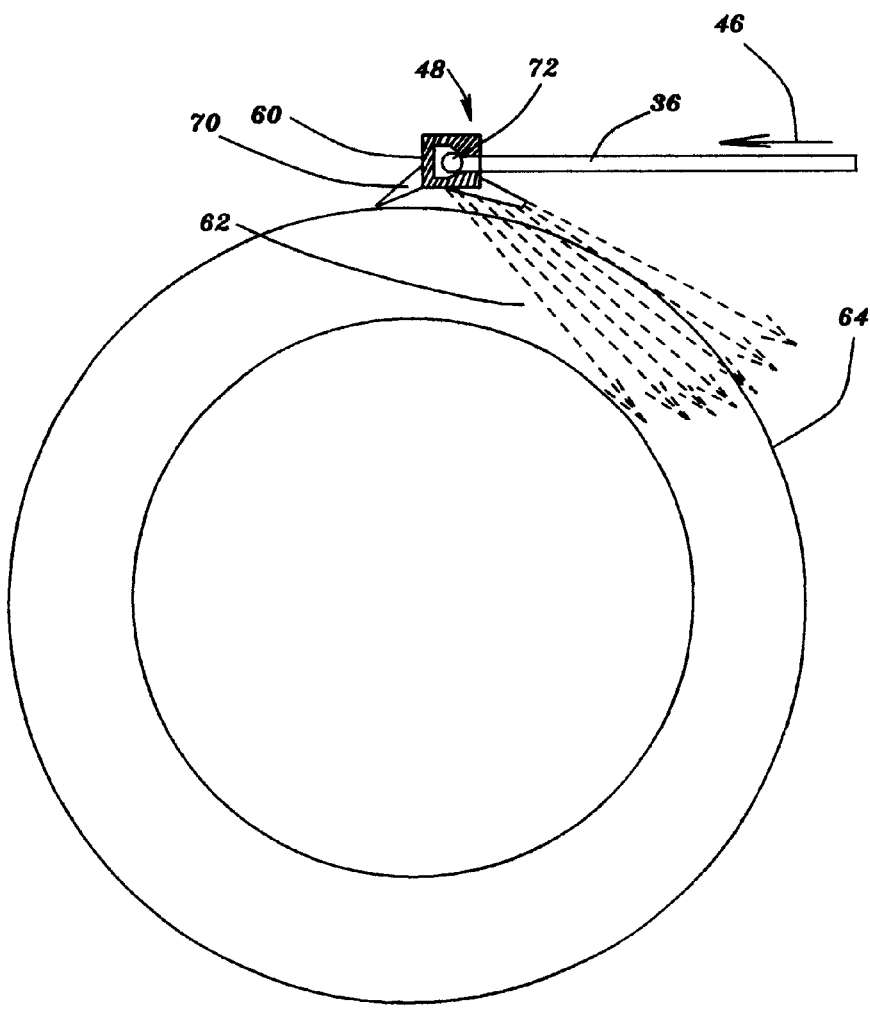
FIG. 4 is an enlarged side elevational view of one of the tires of the vehicle shown in FIG. 1 showing the spray nozzle.

FIG. 4 is an enlarged side elevational view of one of the nozzles 48. As shown in FIG. 4, each of the fan pattern sprays such as 60, includes a shield 70 for protecting the fan pattern spray 60. Also, each of the fan pattern sprays 60 and 66 respectively includes an anti-drip check valve 72 which preferably is a one way flow valve for maintaining the fan pattern spray 60 and 66 respectively primed with the disinfectant 14.

Also, in a preferred embodiment of the present invention, as shown in FIG. 1, the apparatus 10 includes a further flow line 74 extending from the pump 22 and a valve 76 operatively disposed along the further flow line 74 for controlling flow of the disinfectant 14 through the further flow line 74 when the switch 28 is disposed in an operative disposition thereof. The valve 76 has an open and a closed disposition so that when the valve 76 is disposed in the open disposition thereof spraying of a driver's footwear is permitted.

Additionally, in a preferred embodiment of the present invention, as shown in FIG. 3, the apparatus 10 includes a Global Positioning System (GPS) 78 for ascertaining a location of the vehicle 12 when the tires 15–18 are being sprayed. The apparatus 10 also includes a recording device 80 connected to the GPS 78 for recording the location of the vehicle 12 and the time when the vehicle 12 enters and leaves the farm.

Figure 5:
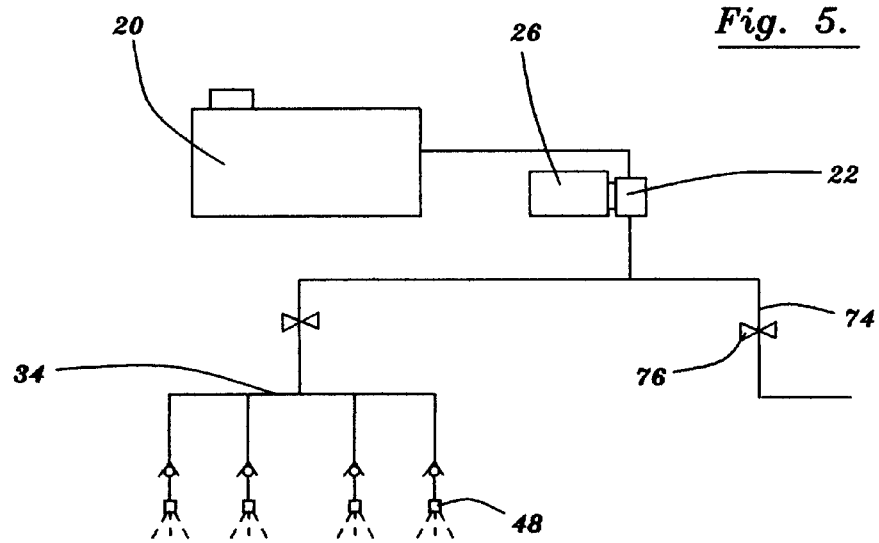
FIG. 5 is a schematic representation of the disinfectant spraying apparatus shown in FIG. 1.

FIG. 5 is a schematic representation of the disinfectant spraying apparatus shown in FIG. 1. As shown in FIG. 5, the pump 22 pumps the disinfectant to four spray nozzles 48. However, if the vehicle has more than four wheels, more spray nozzles can be provided.

Figure 6:
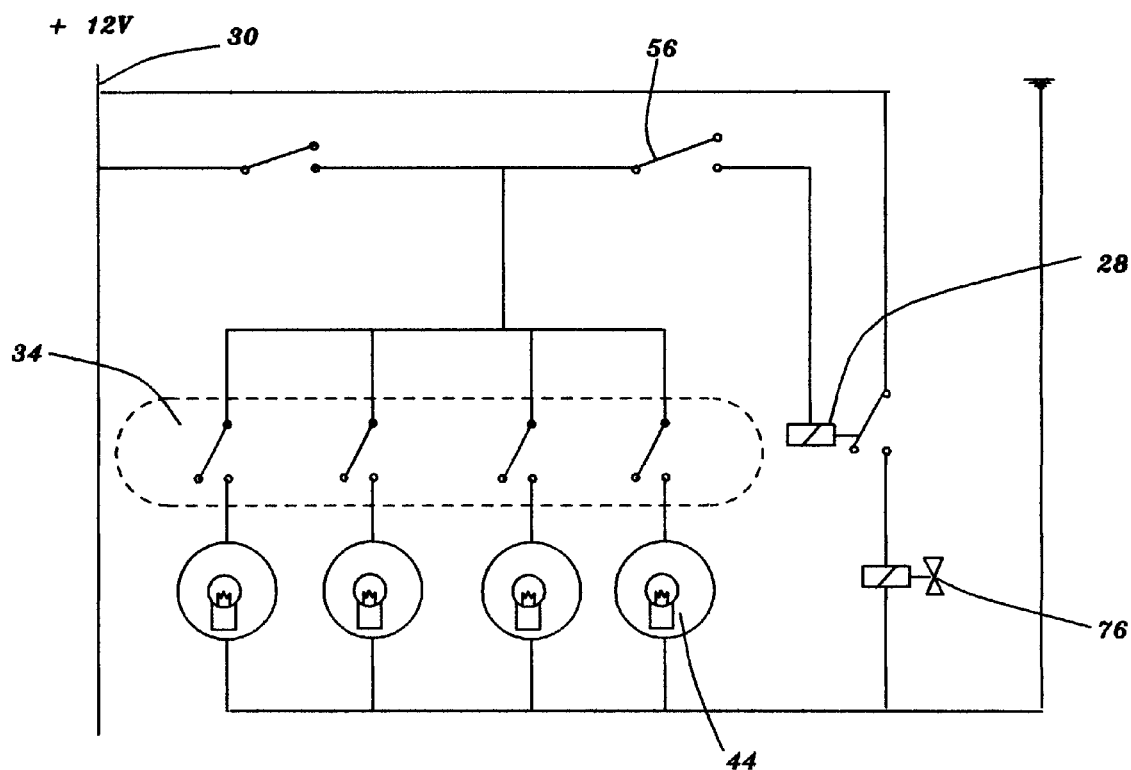
FIG. 6 is an electrical circuit diagram for the disinfectant spraying apparatus shown in FIG.

FIG. 6 is an electrical circuit diagram for the disinfectant spraying apparatus 10 shown in FIG. 1. As shown in FIG. 6, the splitter 34 can include a number of flow switches which energize the LED indicators when disinfectant is flowing through the flow line.

In operation of the apparatus 10 according to the present invention, when the driver of the vehicle 12 approaches a farm, the driver pushes the actuator 54 so that the pump 22 pumps disinfectant 14 to each of the tires 15–18. The timer 56 can be adjusted by the adjuster 58 so that the tires are sprayed for a minute or so as the vehicle approaches and enters the farm. Also, the further flow line 74 may be used to spray the driver's boots before the driver makes an exit from the vehicle. Alternatively, the flow line 74 may supply disinfectant to a footbath (not shown) for disinfecting the driver's footwear.

Furthermore, when the vehicle is leaving the farm, the actuator 54 is pushed by the driver so that the tires are again sprayed so that if any infection exists at the farm, such infection will not be transported on the tires 15–18 to another farm.

The GPS 78 is provided for automatically recording the location of the vehicle 12 when the actuator 54 is pushed. Also, the recording device 80 retains a record of the time and location when the tires were sprayed.

The present invention provides a unique apparatus for fitting onto a vehicle for inhibiting the spread of contagious diseases between farms.

What is claimed is:

1. A disinfectant spraying apparatus mounted on a vehicle for spraying disinfectant on each tire of a vehicle before and after entering a livestock farm, said apparatus comprising:
    a container for containing the disinfectant, said container being mounted on the vehicle;
    a pump disposed in fluid communication with said container for pumping the disinfectant from said container;
    a motor for driving said pump;
    a manually operated switch for selectively connecting said motor to a source of power such that when said switch is disposed in an operative disposition thereof, said motor is energized so that said motor drives said pump for generating a flow of the disinfectant downstream from said pump;
    a flow splitter for splitting said flow of the disinfectant pumped by said pump from said container such that said flow is split into a plurality of flow lines, each flow line of said plurality of flow lines having an upstream and a downstream end;
    an indicator connected between said upstream and downstream ends of each flow line for indicating flow of the disinfectant through said flow line; and
    a spray nozzle disposed adjacent to said downstream end of each flow line, said nozzle being located in a vicinity of a tire of the vehicle so that the vehicle tire is initially sprayed with the disinfectant prior to entry of the vehicle into the farm for inhibiting the spread of contagious disease into the farm and for further spraying the vehicle tire when the vehicle leaves the farm.

2. A disinfectant spraying apparatus as set forth in claim 1 wherein said container is of rectangular configuration.

3. A disinfectant spraying apparatus as set forth in claim 1 wherein said container is fabricated from polypropylene.

4. A disinfectant spraying apparatus as set forth in claim 1 wherein said container has a capacity within the range 6–12 gallons.

5. A disinfectant spraying apparatus as set forth in claim 1 wherein said pump has a flow capacity within the range 2–4 gallons per minute.

6. A disinfectant spraying apparatus as set forth in claim 1 wherein said pump includes:
    a diaphragm.

7. A disinfectant spraying apparatus as set forth in claim 1 wherein said motor is a 12 volt D.C. electric motor.

8. A disinfectant spraying apparatus as set forth in claim 1 further including: a control panel.

9. A disinfectant spraying apparatus as set forth in claim 8 wherein said manually operated switch is mounted on said control panel.

10. A disinfectant spraying apparatus as set forth in claim 8 wherein said indicator is mounted on said control panel.

11. A disinfectant spraying apparatus as set forth in claim 1 wherein said manually operated switch includes:
    a push button actuator.

12. A disinfectant spraying apparatus as set forth in claim 1 further including:
    a timer connected to said manually operated switch so that said timer throws said switch from said operative disposition to an inoperative disposition thereof after a period of time.

13. A disinfectant spraying apparatus as set forth in claim 12 wherein said timer includes:
    an adjuster for adjusting said period of time.

14. A disinfectant spraying apparatus as set forth in claim 1 wherein said flow splitter splits said flow into four flow lines for spraying each tire of the vehicle.

15. A disinfectant spraying apparatus as set forth in claim 1 wherein said indicator is a LED indicator light.

16. A disinfectant spraying apparatus as set forth in claim 1 wherein said spray nozzle includes:
    a first fan pattern spray for spraying an outer wall and tread of one of the tires;
    a second fan pattern spray for spraying an inner wall and tread of the one of the tires.

17. A disinfectant spraying apparatus as set forth in claim 16 wherein each of said fan pattern sprays includes:
    a shield for protecting said fan pattern spray.

18. A disinfectant spraying apparatus as set forth in claim 16 wherein each of said fan pattern sprays includes:
    an anti-drip check valve.

19. A disinfectant spraying apparatus as set forth in claim 18 wherein said anti-drip check valve is a one way flow valve which maintains said fan pattern spray primed with the disinfectant.

20. A disinfectant spraying apparatus mounted on a vehicle for spraying disinfectant on each tire of a vehicle before and after entering a livestock farm, said apparatus comprising:
    a container for containing the disinfectant, said container being mounted on the vehicle;
    a pump disposed in fluid communication with said container for pumping the disinfectant from said container;
    a motor for driving said pump;
    a manually operated switch for selectively connecting said motor to a source of power such that when said switch is disposed in an operative disposition thereof, said motor is energized so that said motor drives said pump for generating a flow of the disinfectant downstream from said pump;
    a flow splitter for splitting said flow of the disinfectant pumped by said pump from said container such that said flow is split into a plurality of flow lines, each flow line of said plurality of flow lines having an upstream and a downstream end; an indicator disposed between said upstream and downstream ends of each flow line for indicating flow of the disinfectant through said flow line;
    a spray nozzle disposed adjacent to said downstream end of each flow line, said nozzle being located in a vicinity of a tire of the vehicle so that the vehicle tire is initially sprayed with the disinfectant prior to entry of the vehicle into the farm for inhibiting the spread of contagious disease into the farm and for further spraying the vehicle tire when the vehicle leaves the farm;
    a further flow line extending from said pump; and
    a valve operatively disposed along said further flow line for controlling flow of the disinfectant through said further flow line when said switch is disposed in said operative disposition thereof, said valve having an open and a closed disposition so that when said valve is disposed in said open disposition thereof spraying of a driver's footwear is permitted.

21. A disinfectant spraying apparatus mounted on a vehicle for spraying disinfectant on each tire of a vehicle before and after entering a livestock farm, said apparatus comprising:

a container for containing the disinfectant, said container being mounted on the vehicle;

a pump disposed in fluid communication with said container for pumping the disinfectant from said container;

a motor for driving said pump;

a manually operated switch for selectively connecting said motor to a source of power such that when said switch is disposed in an operative disposition thereof, said motor is energized so that said motor drives said pump for generating a flow of the disinfectant downs from said pump;

a flow splitter for splitting said flow of the disinfectant pumped by said pump from said container such that said flow is split into a plurality of flow lines, each flow line of said plurality of flow lines having an upstream and a downstream end;

an indicator disposed between said upstream and downstream ends of each flow line for indicating flow of the disinfectant through said flow line;

a spray nozzle disposed adjacent to said downstream end of each flow line, said nozzle being located in a vicinity of a tire of the vehicle so that the vehicle tire is initially sprayed with the disinfectant prior to entry of the vehicle into the farm for inhibiting the spread of contagious disease into the farm and for further spraying the vehicle tire when the vehicle leaves the farm;

a GPS for ascertaning a location of the vehicle when the tires are being sprayed; and a recording device connected to said GPS for recording said location of the vehicle and the time when the vehicle enters and leaves the farm.

* * * * *